United States Patent [19]

Morozowich

[11] 3,968,140

[45] July 6, 1976

[54] SUBSTITUTED ANILIDE ESTERS OF $PGE_1$

[75] Inventor: Walter Morozowich, Kalamazoo, Mich.

[73] Assignee: The Upjohn Company, Kalamazoo, Mich.

[22] Filed: Jan. 8, 1974

[21] Appl. No.: 431,599

[52] U.S. Cl............................................. 260/468 D
[51] Int. Cl.² ................ C07C 133/08; C07C 103/82
[58] Field of Search ................................ 260/468 D

[56] References Cited
FOREIGN PATENTS OR APPLICATIONS
775,106   3/1972   Belgium .............................. 260/468

OTHER PUBLICATIONS
Fieser et al., Reagent For Organic Synthesis pp. 86, 1229 (1967).

*Primary Examiner*—Robert Gerstl
*Attorney, Agent, or Firm*—Morris L. Nielsen

[57] ABSTRACT

Substituted phenyl and naphthyl esters of $PGE_1$, 15-alkyl-$PGE_1$, and 15(R)-15-alkyl-$PGE_1$, and their racemic forms, and processes for producing them are disclosed. The products are useful for the same pharmacological and medical purposes as $PGE_1$, 15-alkyl-$PGE_1$, and 15(R)-15-alkyl-$PGE_1$, and are also useful as a means for obtaining highly purified $PGE_1$, 15-alkyl-$PGE_1$, and 15(R)-15-alkyl-$PGE_1$ products.

10 Claims, No Drawings

SUBSTITUTED ANILIDE ESTERS OF PGE

BACKGROUND OF THE INVENTION

This invention relates to novel ester derivatives of prostaglandin E₁ (hereinafter identified as "PGE₁"), 15-alkyl-PGE₁, 15(R)-15-alkyl-PGE₁, and their racemic forms, and to processes for producing them.

PGE₁ is represented by the formula:

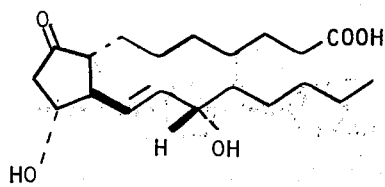

A systematic name for PGE₁ is 7-{3α-hydroxy-2β-[(3S)-3-hydroxy-trans-1-octenyl]-5-oxo-1α-cyclopentyl}-heptanoic acid. PGE₁ is known to be useful for a variety of pharmacological and medical purposes, for example labor induction and abortion in pregnant animals, including humans, menstrual regulation in both pregnant and non-pregnant animals, including humans, reduction and control of gastric secretion, and as a hypotensive agent to reduce blood pressure in mammals, including humans. See Bergstrom et al., Pharmacol. Rev. 20, 1 (1968) and references cited therein. As to racemic PGE₁, see for example W. P. Schneider et al., J. Am. Chem. Soc. 91, 5372 (1969).

The 15-alkyl-PGE₁ analog and its 15(R) epimer are represented by the formula:

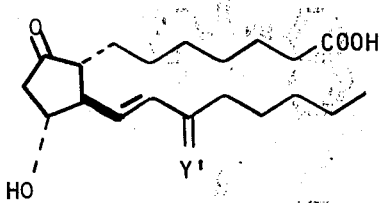

wherein Y' is

following the usual convention wherein broken line attachment of hydroxy to the side chain at carbon 15 indicates the natural or "S" configuration and solid line attachment of hydroxy indicates the epi or "R" configuration. See for example Nugteren et al., Nature 212, 38 (1966) and Cahn, J. Chem. Ed. 41, 116 (1964). The 15-alkyl- and 15(R)-15-alkyl-PGE₁ analogs in their optically active and racemic forms are known. See for example U.S. Pat. No. 3,728,382. These analogs are also useful for the above-described pharmacological purposes.

Esters of the above compounds are known, wherein the hydrogen atom of the carboxyl group is replaced by a hydrocarbyl or substituted hydrocarbyl group. Among these are the methyl ester of PGE₁ (B. Samuelsson, J. Biol. Chem. 238, 3229 (1963)), see also U.S. Pat. No. 3,069,322), the methyl esters of 15-methyl-PGE₁ and dl-15-methyl-PGE₁ (G. L. Bundy et al., Ann. N.Y. Acad. Sci. 180, 76 (1976)), the ethyl ester of PGE₁ (R. Ryhage et al., Biochem. Biophys. Res. Commun. 19, 279 (1965)), and the octafluoro-1-pentyl ester of PGE₁ (Belgian Patent 775,106, Derwent Farmdoc No. 33705T).

SUMMARY OF THE INVENTION

It is a purpose of this invention to provide novel ester derivatives of prostaglandin PGE₁, 15-alkyl-PGE₁, 15(R)-15-alkyl-PGE₁, and their racemic forms. It is a further purpose to provide such esters derived from substituted phenols and naphthols. It is a further purpose to provide such esters in a free-flowing crystalline form. It is still a further purpose to provide novel processes for preparing these esters.

The presently described esters include compounds represented by the generic formula:

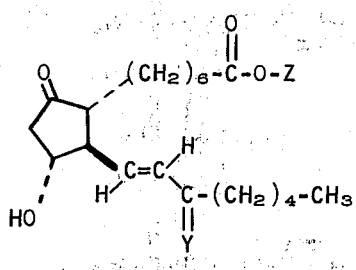

III wherein Z is the substituted phenyl or naphthyl group as defined immediately below, and Y is

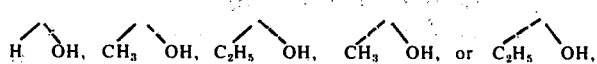

i.e. esters of PGE₁, 15-methyl-PGE₁, and 15(R)-15-methyl-PGE₁, 15-ethyl-PGE₁, and 15(R)-15-ethyl-PGE₁, and also the racemic compounds represented by each respective formula and the mirror image thereof; Z being represented by

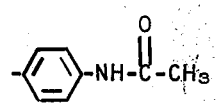  A

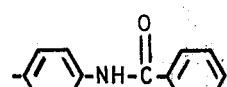  B

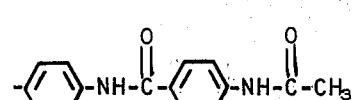  C

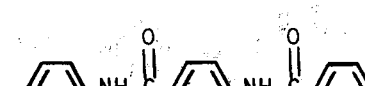  D

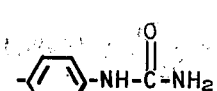  E

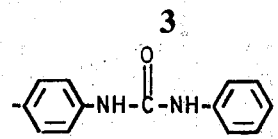 F
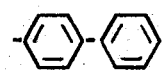 G
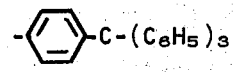 H
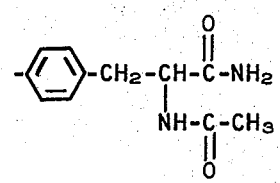 I
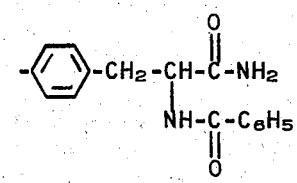 J
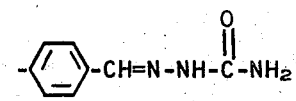 K
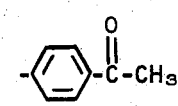 L
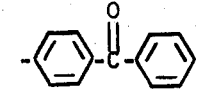 M
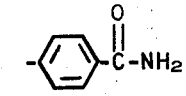 N
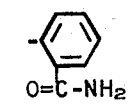 O
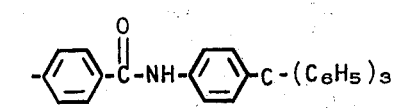 P
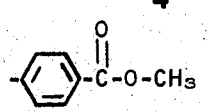 Q
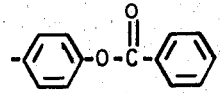 R
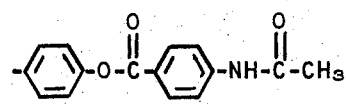 S
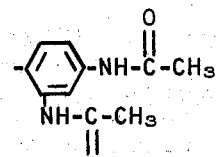 T
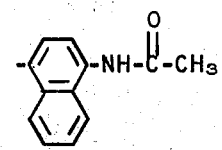 U
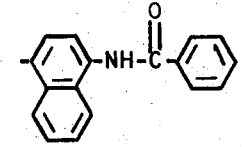 V
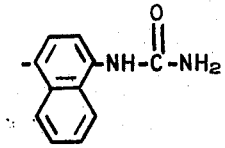 W
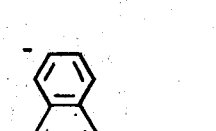 X
or
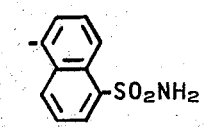 Y
For example, PGE$_1$, p-acetamidophenyl ester, is represented by formula III when Y is

and Z is A, i.e.

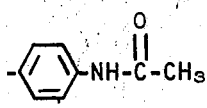

and is conveniently identified herein as the PGE$_1$ ester of formula III-A. Racemic compounds are designated by the prefix "racemic" or "dl"; when that prefix is absent, the intent is to designate an optically active compound. Racemic 15-methyl-PGE$_1$, p-benzamidophenyl ester, corresponds to formula III wherein Y is

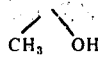

and Z is B, i.e.

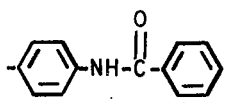

including of course not only the optically active isomer represented by formula III but also its mirror image.

The novel formula-III compounds and corresponding racemic compounds of this invention are each useful for the same purposes as described above for PGE$_1$ and are used for those purposes in the same manner known in the art, including oral, sublingual, buccal, rectal, intravaginal, intrauterine, or topical administration.

For many applications these novel prostaglandin esters which I have obtained from certain specified phenols and naphthols have advantages over the corresponding known prostaglandin compounds. Thus, these substituted phenyl and naphthyl esters are surprisingly stable compounds having outstanding shelf-life and thermal stability. In contrast to the acid form of these prostaglandins, these esters are not subject to acid-catalyzed decomposition either by elimination of water or by epimerization. Thus these compounds have improved stability either in solid, liquid, or solution form. In oral administration these esters have shown surprisingly greater efficacy than the corresponding free acids or lower alkyl esters, whether because of longer duration of biological activity or because of improved lipophilicity and absorption is not certain. These esters offer a further advantage in that they have low solubility in water and the body fluids are therefore retained longer at the site of administration.

A particularly outstanding advantage of many of these substituted phenyl and naphthyl esters is that they are obtained in free-flowing crystalline form, generally of moderately high melting point, in the range 90°–180° C. This form is especially desirable for ease of handling, administering, and purifying. These crystals are highly stable, for example showing practically no decomposition at accelerated storage tests at 65° C., in comparison with liquid alkyl esters or the free acids. This quality is advantageous because the compound does not lose its potency and does not become contaminated with decomposition products.

These crystalline esters also provide a means of purifying PGE$_1$, 15-methyl-PGE$_1$, 15(R)-15-methyl-PGE$_1$, 15-ethyl-PGE$_1$, or 15(R)-15-ethyl-PGE$_1$, which are first converted to one of these esters, recrystallized until pure, and then recovered as the free acid. One method of recovering the free acid is by enzymatic hydrolysis of the ester, for example with a lipase. See German Patent 2,242,792, Derwent Farmdoc No. 23047U.

To obtain the optimum combination of stability, duration of biological activity, lipophilicity, solubility, and crystallinity, certain compounds within the scope of formula III are preferred.

One preference is that Z is limited to either

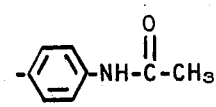

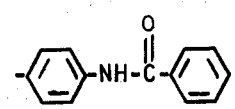

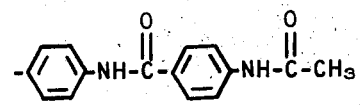

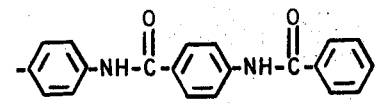

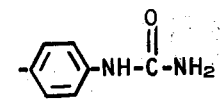

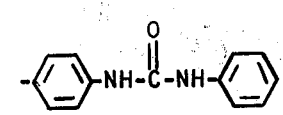

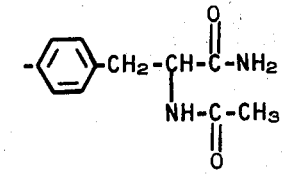

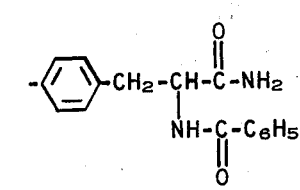

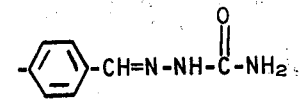

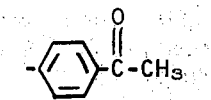
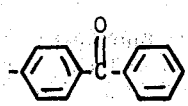
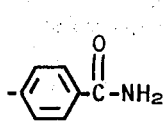
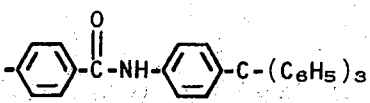
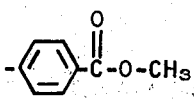
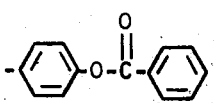
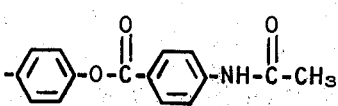
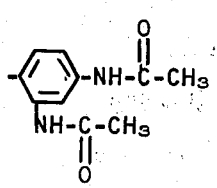
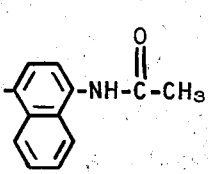
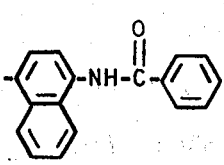
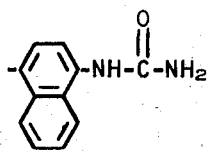
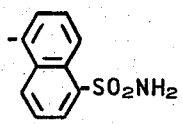
Another preference is that Z is further limited to
(1) 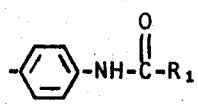
wherein $R_1$ is
−CH₃
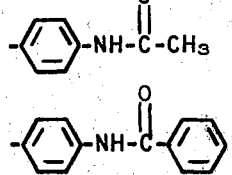
−NH₂
−NH−⟨⟩ ;
(2) 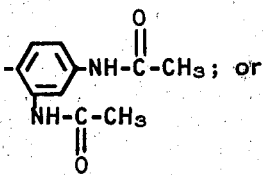 ; or
(3) 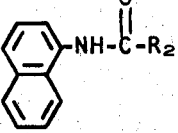
wherein $R_2$ is     −CH₃
−⟨⟩ or
−NH₂ .

Another preference is that Z is limited to $$-\phenyl-CH_2-CH(NH-C(=O)-CH_3)-C(=O)-NH_2$$

$$-\phenyl-CH_2-CH(NH-C(=O)-C_6H_5)-C(=O)-NH_2$$

or $$-\phenyl-CH=N-NH-C(=O)-NH_2.$$

Another preference is that Z is limited to (1)

$$-\phenyl-C(=O)-R_3$$

wherein $R_3$ is

—$CH_3$ $\phenyl$

—$NH_2$

-NH-$\phenyl$-C-(C_6H_5)_3  or

O—$CH_3$;

or (2)

$$-\phenyl-O-C(=O)-R_4,$$

wherein $R_4$ is

-$\phenyl$  or

-$\phenyl$-NH-C(=O)-CH_3.

Especially preferred ae those compounds which are in free-flowing crystalline form, for example:
 p-acetamidophenyl ester of $PGE_1$ or
 p-benzamidophenyl ester of $PGE_1$.

The substituted phenyl and naphthyl esters of $PGE_1$, 15-alkyl-$PGE_1$, and 15(R)-15-alkyl-$PGE_1$, encompassed by formula III wherein Z is defined by ester groups A through Y are produced by the reactions and procedures described and exemplified hereinafter. For convenience, the above prostaglandin or prostaglandin analog is referred to as "the PG compound". The term "phenol" is used in a generic sense, including both phenols and naphthols.

Various methods are available for preparing these esters, differing as to yield and purity of product. Thus, by one method, the PG compound is converted to a tertiary amine salt, reacted with pivaloyl halide to give the mixed acid anhydride and then reacted with the phenol. Alternately, instead of pivaloyl halide, an alkyl or phenylsulfonyl halide is used, such as p-toluenesulfonyl chloride. See for example Belgian patents 775,106 and 776,294, Derwent Farmdoc Nos. 33705T and 39011T.

Still another method is by the use of the coupling reagent, dicyclohexylcarbodiimide. See Fieser et al., "Reagents for Organic Synthesis", pp. 231–236, John Wiley and Sons, Inc., New York (1967). The PG compound is contacted with one to ten molar equivalents of the phenol in the presence of 2–10 molar equivalents of dicyclohexylcarbodiimide in pyridine as a solvent.

The preferred novel process for the preparation of these esters, however, comprises the steps (1) forming a mixed anhydride with the PG compound and isobutylchloroformate in the presence of a tertiary amine and (2) reacting the anhydride with an appropriate phenol and naphthol.

The mixed anhydride is represented by the formula:

$$\text{[cyclopentane ring with HO, =O, side chains]} -C(=O)-O-C(=O)-O-CH_2-CH(CH_3)_2 \quad IV$$

for the optically active PG compounds, Y having the same definition as above.

The anhydride is formed readily at temperatures in the range −40° to +60° C., preferably at −10° to +10° C. so that the rate is reasonably fast and yet side reactions are minimized. The isobutylchloroformate reagent is preferably used in excess, for example 1.2 molar equivalents up to 4.0 mole of the PG compound. The reaction is preferably done in a solvent and for this purpose acetone is preferred, although other relatively non-polar solvents are used such as acetonitrile, dichloromethane, and chloroform. The reaction is run in the presence of a tertiary amine, for example triethylamine, and the co-formed amine hydrochloride usually crystallizes out, but need not be removed for the next step.

The anhydride is usually not isolated but is reacted directly in solution with the phenol, preferably in the presence of a tertiary amine such as pyridine.

The phenol is preferably used in equivalent amounts or in excess to insure that all of the mixed anhydride is converted to ester. Excess phenol is separated from the product by methods described herein or known in the art, for example crystallization. The tertiary amine is not only a basic catalyst for the esterification but also a convenient solvent. Other examples of tertiary amines useful for this purpose include N-methylmorpholine, triethylamine, diisopropylethylamine, and dimethylaniline. Although they may be used, 2-methylpyridine and quinoline result in a slow reaction. A highly hindered amine such as 2,6-dimethyllutidine is not useful because of the slowness of the reaction.

The reaction with the anhydride proceeds smoothly at room temperature (about 20° to 30° C.) and can be followed in the conventional manner with thin layer chromatography (TLC), usually being found complete within 1–4 hours.

The reaction mixture is worked up to yield the ester following methods known in the art, and the product is purified, for example by silica gel chromatography.

Solid esters are converted to a free-flowing crystalline form on crystallization from a variety of solvents, including ethyl acetate, tetrahydrofuran, methanol, and acetone, by cooling or evaporating a saturated solution of the ester in the solvent or by adding a miscible non-solvent such as diethyl ether, hexane, or water. The crystals are then collected by conventional techniques, e.g. filtration or centrifugation, washed with a small amount of solvent, and dried under reduced pressure. They may also be dried in a current of warm nitrogen or argon, or by warming to about 75° C. Although the crystals are normally pure enough for many applications, they may be recrystallized by the same general techniques to achieve improved purity after each recrystallization.

DESCRIPTION OF THE PREFERRED EMBODIMENTS

The invention can be more fully understood by the following examples.

All temperatures are in degrees centigrade.

Silica gel chromatography, as used herein, is understood to include chromatography on a column packed with silica gel, elution, collection of fractions, and combination of those fractions shown by thin layer chromatography (TLC) to contain the desired product free of starting material and impurities.

"TLC", herein, refers to thin layer chromatography.

PREPARATION 1 p-Benzamidophenol

A solution of p-hydroxyaniline (20 g.) in 200 ml. pyridine is treated with benzoic anhydride (20 g.) After 4 hr. at about 25° C., the mixture is concentrated under reduced pressure and the residue is taken up in 200 ml. of hot methanol and reprecipitated with 300 ml. of water. The product is recrystallized from hot acetonitrile as white crystals, 8.5 g., m.p. 218.0°–218.5° C.

PREPARATION 2 p-(p-Acetamidobenzamido)phenol

A solution of p-acetamidobenzoic acid (12.5 g.) in 250 ml. of tetrahydrofuran is treated with triethylamine (11.1 ml.). The mixture is then treated with isobutylchloroformate (10.4 ml.) and, after 5 min. at about 25° C., with p-aminophenol (13.3 g.) in 80 ml. of dry pyridine. After 40 min. the crude product is obtained by addition of 2 liters of water. The product is recrystallized from 500 ml. of hot methanol by dilution with 300 ml. of water as white crystals, 5.9 g., m.p. 275.0°–277.0° C.

EXAMPLE 1 p-Acetamidophenyl Ester of $PGE_1$ (Formula III-A).

A solution of $PGE_1$ (0.450 g.) and triethylamine (0.214 ml.) in 20 ml. of acetone is treated at −20° C. with isobutylchloroformate (0.20 ml.) whereupon triethylamine hydrochloride is precipitated. After 5 min. the mixture is treated with p-acetamidophenol (0.260 g.) in 10 ml. of pyridine for 2 hr. at about 25° C. The solvent is removed under reduced pressure and the residue is dissolved in ethyl acetate and washed with water. The organic phase is dried over sodium sulfate, concentrated, and subjected to silica gel chromatography, eluting with ethyl acetate followed by acetonitrile. The residue obtained by concentration of selected fractions, a solid on chilling, is the title compound, 0.600 g., having $R_f$ 0.3 (TLC on silica gel in ethyl acetate-acetic acid, 97:3). It is recrystallized from ethyl acetate-hexane as white free-flowing crystals, m.p. 133.8°–136.3° C.

EXAMPLE 2 p-Benzamidophenyl Ester of $PGE_1$ (Formula III-B).

Following the procedure of Example 1 but using 0.490 g.

Following the procedure of Example 1 but using 0.490 g. of $PGE_1$, 0.230 ml. of triethylamine, 0.216 ml. of isobutylchloroformate, and 0.400 g. of p-benzamidophenol there is obtained a crude solid residue. This residue is subjected to silica gel chromatography, eluting with ethyl acetate, then ethyl acetate-acetonitrile (1:1), and finally acetonitrile. The residue obtained by concentration of selected fractions, 0.496 g., is crystallized from acetone diluted with 1.5 volumes of hexane as the title compound, 0.356 g., white free-flowing crystals, m.p. 150.8°–154.8° C., having $R_f$ 0.6 (TLC on silica gel in ethyl acetate).

Following the procedures of Examples 1-2 but employing the racemic forms of the PG compounds, there are obtained the corresponding esters of racemic PG compounds.

EXAMPLES 3–75

The substituted phenyl and naphthyl esters of $PGE_1$, 15-methyl-$PGE_1$, and 15(R)-15-methyl-$PGE_1$ of Tables I-III below are obtained following the procedures of Example 1, wherein the prostaglandin compound is reacted in the presence of triethylamine and isobutylchloroformate with the appropriate hydroxy phenyl or naphthyl compound, listed in the Table. These phenols or naphthols are readily available or prepared by methods described herein or known in the art. The crude products, obtained by concentration under reduced pressure, are purified by means described herein or known in the art, including partitioning, solvent extraction, washing, silica gel chromatography, trituration, or crystallization.

Following the procedures of Examples 3–75 but employing the racemic forms of the PG compounds, there are obtained the corresponding esters of the racemic PG compounds.

TABLE I

| Ex. | Hydroxy Phenyl or Naphthyl Compound | Product $PGE_1$ ester of formula: |
|---|---|---|
| | Esters of $PGE_1$ | |
| 3 | p(p-acetamidobenzamido)phenol | III-C |

TABLE I-continued

Esters of PGE₁

| Ex. | Hydroxy Phenyl or Naphthyl Compound | Product PGE₁ ester of formula: |
|---|---|---|
| 4 | p-(p-benzamidobenzamido)phenol | III-D |
| 5 | p-hydroxyphenylurea | III-E |
| 6 | p-hydroxy-1,3-diphenylurea | III-F |
| 7 | p-phenylphenol | III-G |
| 8 | p-tritylphenol | III-H |
| 9 | N-acetyl-L-tyrosinamide | III-I |
| 10 | N-benzoyl-L-tyrosinamide | III-J |
| 11 | p-hydroxybenzaldehyde semicarbazone | III-K |
| 12 | p-hydroxyacetophenone | III-L |
| 13 | p-hydroxybenzophenone | III-M |
| 14 | p-hydroxybenzamide | III-N |
| 15 | o-hydroxybenzamide | III-O |
| 16 | N-(p-tritylphenyl)-p-hydroxybenzamide | III-P |
| 17 | p-hydroxybenzoic acid, methyl ester | III-Q |
| 18 | hydroquinone benzoate | III-R |
| 19 | hydroquinone, p-acetamido-benzoic acid ester | III-S |
| 20 | 2,4-diacetamidophenol | III-T |
| 21 | 1-acetamido-4-hydroxy-naphthalene | III-U |
| 22 | 1-benzamido-4-hydroxy-naphthalene | III-V |
| 23 | 1-hydroxy-4-ureido-naphthalene | III-W |
| 24 | 2-naphthol | III-X |
| 25 | 1-hydroxy-5-naphthalene-sulfonamide | III-Y |

TABLE II

Esters of 15-Methyl-PGE₁

| Ex. | Hydroxy Phenyl or Naphthyl Compound | Product 15-Methyl-PGE₁ Ester of formula: |
|---|---|---|
| 26 | p-acetamidophenol | III-A |
| 27 | p-benzamidophenol | III-B |
| 28 | p-(p-acetamidobenzamido)phenol | III-C |
| 29 | p-(p-benzamidobenzamido)phenol | III-D |
| 30 | p-hydroxyphenylurea | III-E |
| 31 | p-hydroxy-1,3-diphenylurea | III-F |
| 32 | p-phenylphenol | III-G |
| 33 | p-tritylphenol | III-H |
| 34 | N-acetyl-L-tyrosinamide | III-I |
| 35 | N-benzoyl-L-tyrosinamide | III-J |
| 36 | p-hydroxybenzaldehyde semicarbazone | III-K |
| 37 | p-hydroxyacetophenone | III-L |
| 38 | p-hydroxybenzophenone | III-M |
| 39 | p-hydroxybenzamide | III-N |
| 40 | o-hydroxybenzamide | III-O |
| 41 | N-(p-tritylphenyl)-p-hydroxybenzamide | III-P |
| 42 | p-hydroxybenzoic acid, methyl ester | III-Q |
| 43 | hydroquinone benzoate | III-R |
| 44 | hydroquinone, p-acetamido-benzoic acid ester | III-S |
| 45 | 2,4-diacetamidophenol | III-T |
| 46 | 1-acetamido-4-hydroxynaphthalene | III-U |
| 47 | 1-benzamido-4-hydroxynaphthalene | III-V |
| 48 | 1-hydroxy-4-ureidonaphthalene | III-W |
| 49 | 2-naphthol | III-X |
| 50 | 1-hydroxy-5-naphthalene-sulfonamide | III-Y |

TABLE III

Esters of 15(R)-15-Methyl-PGE₁

| Ex. | Hydroxy Phenyl or Naphthyl Compound | Product 15(R)-15-Methyl-PGE₁ Ester of formula: |
|---|---|---|
| 51 | p-acetamidophenol | III-A |
| 52 | p-benzamidophenol | III-B |
| 53 | p-(p-acetamidobenzamido)phenol | III-C |
| 54 | p-(p-benzamidobenzamido)phenol | III-D |
| 55 | p-hydroxyphenylurea | III-E |
| 56 | p-hydroxy-1,3-diphenylurea | III-F |
| 57 | p-phenylphenol | III-G |
| 58 | p-tritylphenol | III-H |
| 59 | N-acetyl-L-tyrosinamide | III-I |
| 60 | N-benzoyl-L-tyrosinamide | III-J |
| 61 | p-hydroxybenzaldehyde semicarbazone | III-K |

TABLE III-continued

Esters of 15(R)-15-Methyl-PGE₁

| Ex. | Hydroxy Phenyl or Naphthyl Compound | Product 15(R)-15-Methyl-PGE₁ Ester of formula: |
|---|---|---|
| 62 | p-hydroxyacetophenone | III-L |
| 63 | p-hydroxybenzophenone | III-M |
| 64 | p-hydroxybenzamide | III-N |
| 65 | o-hydroxybenzamide | III-O |
| 66 | N-(p-tritylphenyl)-p-hydroxybenzamide | III-P |
| 67 | p-hydroxybenzoic acid, methyl ester | III-Q |
| 68 | hydroquinone benzoate | III-R |
| 69 | hydroquinone, p-acetamidobenzoic acid ester | III-S |
| 70 | 2,4-diacetamidophenol | III-T |
| 71 | 1-acetamido-4-hydroxynaphthalene | III-U |
| 72 | 1-benzamido-4-hydroxynaphthalene | III-V |
| 73 | 1-hydroxy-4-ureidonaphthalene | III-W |
| 74 | 2-naphthol | III-X |
| 75 | 1-hydroxy-5-naphthalenesulfonamide | III-Y |

I claim:

1. An optically active compound of the formula:

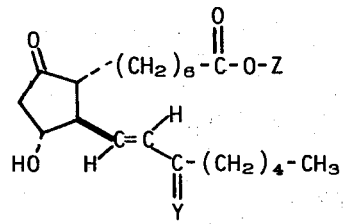

or a racemic compound of that formula and the mirror image thereof, wherein Z is (1) 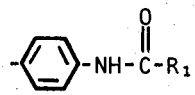

wherein $R_1$ is

-CH₃

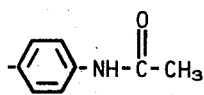

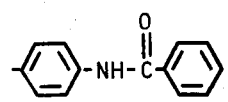

-NH₂ or

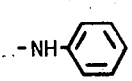

(2) 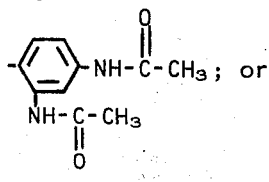 or (3) 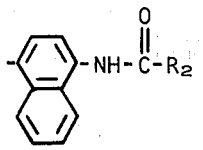

wherein $R_2$ is

-NH$_2$;

and wherein Y is

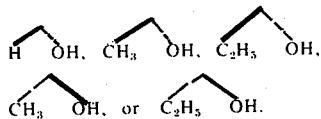

2. The ester of p-hydroxybenzamide and PGE$_1$, a compound according to claim 1.

3. The ester of o-hydroxybenzamide and PGE$_1$, a compound according to claim 1.

4. the ester of p-hydroxyphenylurea and 15-methyl-PGE$_1$, a compound according to claim 1.

5. The ester of 2,4-diacetamidophenol and 15-methyl-PGE$_1$, a compound according to claim 1.

6. The ester of 1-acetamido-4-hydroxynaphthalene and 15-methyl-PGE$_1$, a compound according to claim 1.

7. The ester of 1-hydroxy-4-ureidonaphthalene and 15-methyl-PGE$_1$, a compound according to claim 1.

8. The ester of p-acetamidophenol and PGE$_1$, a compound according to claim 1.

9. The ester of p-benzamidophenol and PGE$_1$, a compound according to claim 1.

10. Free-flowing crystals of a compound of the formula:

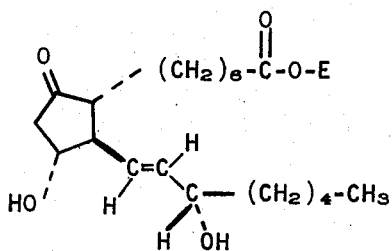

wherein E is

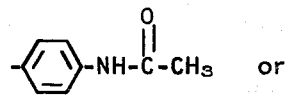 or

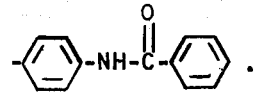 .

* * * * *

Disclaimer 3,968,140.—*Walter Morozowich*, Kalamazoo, Mich. SUBSTITUTED ANI-
LIDE ESTERS OF PGE. Patent dated July 6, 1976. Disclaimer filed
Mar. 14, 1977, by the assignee, *The Upjohn Company*.
Hereby enters this disclaimer to claims 2 and 3 of said patent.
[*Official Gazette May 24, 1977.*]